United States Patent
Hanson et al.

(10) Patent No.: US 7,389,146 B2
(45) Date of Patent: Jun. 17, 2008

(54) SELF-DESCRIBING REAL-TIME DEVICE DATA COMMUNICATION SYSTEM

(75) Inventors: Roland J. Hanson, Forest Lake, MN (US); Christopher M. Petersen, Ham Lake, MN (US); Ruth N. Klepfer, St. Louis Park, MN (US); Marilyn C Rochat, Golden Valley, MN (US); James H. Ericksen, North Oaks, MN (US); Anthony J. Koenigsfeld, Champlin, MN (US); Charles R. Stomberg, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 336 days.

(21) Appl. No.: 10/946,486

(22) Filed: Sep. 21, 2004

(65) Prior Publication Data

US 2006/0020301 A1    Jan. 26, 2006

Related U.S. Application Data

(60) Provisional application No. 60/589,253, filed on Jul. 20, 2004.

(51) Int. Cl.
*A61N 1/00* (2006.01)

(52) U.S. Cl. .................. 607/60; 128/903
(58) Field of Classification Search ............ 607/60; 128/903, 904
See application file for complete search history.

(56) References Cited

U.S. PATENT DOCUMENTS

| 5,383,915 | A * | 1/1995 | Adams ................ 607/60 |
| 5,626,630 | A * | 5/1997 | Markowitz et al. ...... 607/60 |
| 6,250,309 | B1 | 6/2001 | Krichen et al. |
| 6,443,891 | B1 | 9/2002 | Grevious |
| 6,564,104 | B2 | 5/2003 | Nelson et al. |
| 6,583,796 | B2 | 6/2003 | Jamar et al. |
| 6,665,558 | B2 * | 12/2003 | Kalgren et al. ........ 600/510 |
| 7,009,511 | B2 * | 3/2006 | Mazar et al. .......... 340/531 |
| 2001/0023360 | A1 | 9/2001 | Nelson et al. |
| 2002/0082662 | A1 | 6/2002 | Vanderlinde et al. |
| 2003/0109904 | A1 | 6/2003 | Silver et al. |
| 2004/0102687 | A1 | 5/2004 | Brashears et al. |

\* cited by examiner

*Primary Examiner*—Carl H. Layno
*Assistant Examiner*—Brian T Gedeon
(74) *Attorney, Agent, or Firm*—Daniel G. Chapik

(57) ABSTRACT

An implantable medical device (IMD) communicates with an external processing unit by transmitting device data and configuration information that describes the device data. The external processing unit processes the device data for display based on the configuration information. The IMD notifies the external processing unit of a change to characteristics of the device data by transmitting the changed device data and updated configuration information.

12 Claims, 3 Drawing Sheets

SELF-DESCRIBING REAL-TIME DEVICE DATA COMMUNICATION SYSTEM

CROSS-REFERENCE TO RELATED APPLICATION(S)

This application claims the benefit of U.S. Provisional Application No. 60/589,253 filed Jul. 20, 2004 for "Self-Describing Real-Time Device Data Communication System" by R. Hanson, C. Petersen, R. Klepfer, M. Rochat, J. Ericksen, C. Stomberg and A. Koenigsfeld.

INCORPORATION BY REFERENCE

The aforementioned U.S. Provisional Application No. 60/589,253 is hereby incorporated by reference in its entirety.

BACKGROUND OF THE INVENTION

The present invention relates to a system for communicating data between an implantable medical device (IMD) and an external processing unit.

Since the introduction of the first implantable pacemakers in the 1960s, there have been considerable advancements in both the field of electronics and medicine, such that there is presently a wide assortment of commercially available body-implantable electronic medical devices. The class of IMDs now includes pacemakers, implantable cardioverters, defibrillators, neural stimulators, and drug administering devices, among others. Today's state-of-the-art IMDs are vastly more sophisticated and complex than early ones, and are capable of performing significantly more complex tasks. The therapeutic benefits of such devices have been well proven.

It has proven useful for IMDs to have the capability of communicating data with an external processing unit that in turn has the ability to process, store and/or display data provided by the device. The data provided by the device may be real-time or recorded data. The external unit may also transmit signals to the implanted medical device in order to provide some control over the device. This communication is achieved by wireless telemetry, the physical characteristics of which are known in the art.

Existing implantable medical device systems have relied on the external processing unit to initiate data communication with the IMD, at least in part due to processing limitations of the IMD. A typical scenario in such a system is as follows:

(1) "Wake up" implantable device, such as with wireless transmission, a magnet, or other initiating means.

(2) Implantable device transmits device identification information.

(3) External processing unit identifies device and loads appropriate application program.

(4) External processing unit interrogates implantable device to determine configuration of device, such as type or format of data that will be transmitted, etc.

(5) Implantable device transmits data to external processing unit according to format and configuration established.

(6) External processing unit initiates change in data type or format to be transmitted by implantable device by transmitting command to device.

(7) Implantable device adjusts the type or format of the data transmission.

This communication scenario illustrates the necessity, in existing systems, of a specific application program for each type of device and for each data characteristic (data type, structure or format) supported by the device, so that proper manipulation of the raw data transmitted by the implantable device can be done according to the configuration determined by the external processing unit by interrogation. While these systems have provided excellent results in situations where application programs and IMDs are specifically designed to work together, it would be useful to provide a system in which at least some level of data communication and cooperation is available even when the application program is not specifically designed for a particular IMD or data characteristic.

BRIEF SUMMARY OF THE INVENTION

The present invention is a system and technique for communicating between an implantable medical device (IMD) and an external processing unit. The IMD transmits device data and configuration information that describes the device data. The external processing unit processes the device data for display based on the configuration information. The IMD notifies the external processing unit of a change to a characteristic of the device data by transmitting the changed device data and updated configuration information.

DETAILED DESCRIPTION

Figure 1:
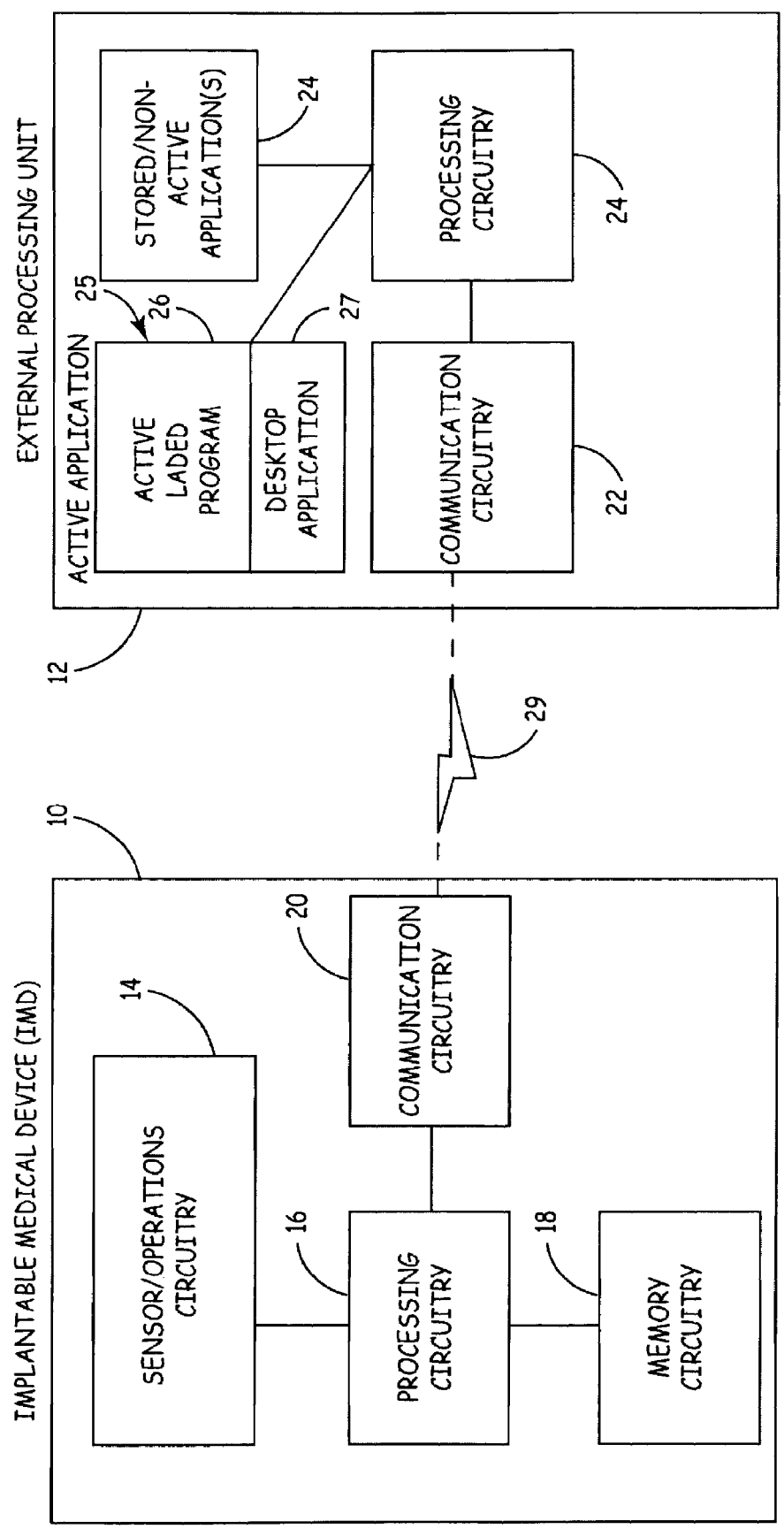
FIG. 1 is a block diagram illustrating the basic functional components of an implantable medical device and an external processing unit.

FIG. 1 is a block diagram illustrating the basic functional components of implantable medical device (IMD) 10 and external processing unit 12. IMD 10 includes sensor/operating circuitry 14, processing circuitry 16, memory circuitry 18, and communication circuitry 20. External processing unit 12 includes communication circuitry 22, processing circuitry 24, active application 25 including active loaded program 26 and desktop application 27, and stored/non-active application(s) 28. Communication circuitry 20 of IMD 10 and communication circuitry 22 of external processing unit 12 communicate with one another over wireless link 29, which may be a radio frequency (RF) link or another suitable type of wireless communication.

In operation, IMD 10 is capable of transmitting data relating to the operation of sensor/operating circuitry 14 and data relating to its configuration stored in memory circuitry 18 over wireless link 29 to external processing unit 12. IMD 10 is also capable of receiving programming information and other communication from external processing unit 12 to control the operation of sensor/operating circuitry 14 and to direct communication between IMD 10 and external processing unit 12. External processing unit 12 is capable of processing the data received from IMD 10 according to an appropriate application program. Specifically, external processing unit 12 receives configuration information from IMD 10, and loads an appropriate application program (active loaded program 26) for execution. Active loaded program 26 is able to properly manipulate and/or display the operation data that is transmitted by IMD 10, while other programs (stored/non-active application(s) 28) that are not suited for manipulation and/or display of the operation data are simply stored and not loaded for execution by external processing unit 12.

As discussed previously, the existing procedure for establishing and adjusting communication of operation data between IMD 10 and external processing unit 12 requires external processing unit 12 to control the communication session, and requires execution of active loaded program 26 in order to properly manipulate and/or display data received from implantable medical device 10. Users are therefore required to wait for external processing unit 12 to load and execute the appropriate application program before any data can be viewed, even though IMD 10 may already be transmitting the data. This often can take 20 seconds or more, which is at the very least an annoyance for the user. Moreover, if an appropriate application program is not available for loading by external processing unit 12, then no manipulation and/or display of data from IMD 10 is possible.

The present invention provides a communication scheme in which operation and configuration data is self-describing. This self-describing data allows each type, structure or format of data to be independently processed by the external processing unit. As a result, a system is configured in which the external processing unit is always able to manipulate and/or display at least some data, regardless of whether a specific application program is available that corresponds exactly to the type of IMD or to the type, structure or format of data being transmitted. For example, desktop application 27 may include sufficient capability to process and display certain basic data transmitted by an IMD. The term "desktop application" refers to any application that is continually executed, often in the background, on a computer system. Desktop applications are typically limited in their capabilities because of the desire to limit the system resources that they require, so that the computer system can execute other applications quickly and smoothly. However, the ability of the present invention to transmit self-describing data from an IMD allows desktop application 27 to process and display as small of a set of data characteristics (data types, structures and formats) as desired, within the limits of the system resources available. Because desktop application 27 is continually running in the background, it can process and display supported data types immediately, without having to wait to load a specific application program. The program that is processing and displaying data, whether it be desktop application 27 or active loaded program 26, may have the ability to adapt to a change in the data characteristics and configuration without necessarily having to switch to another active program.

Figure 2:
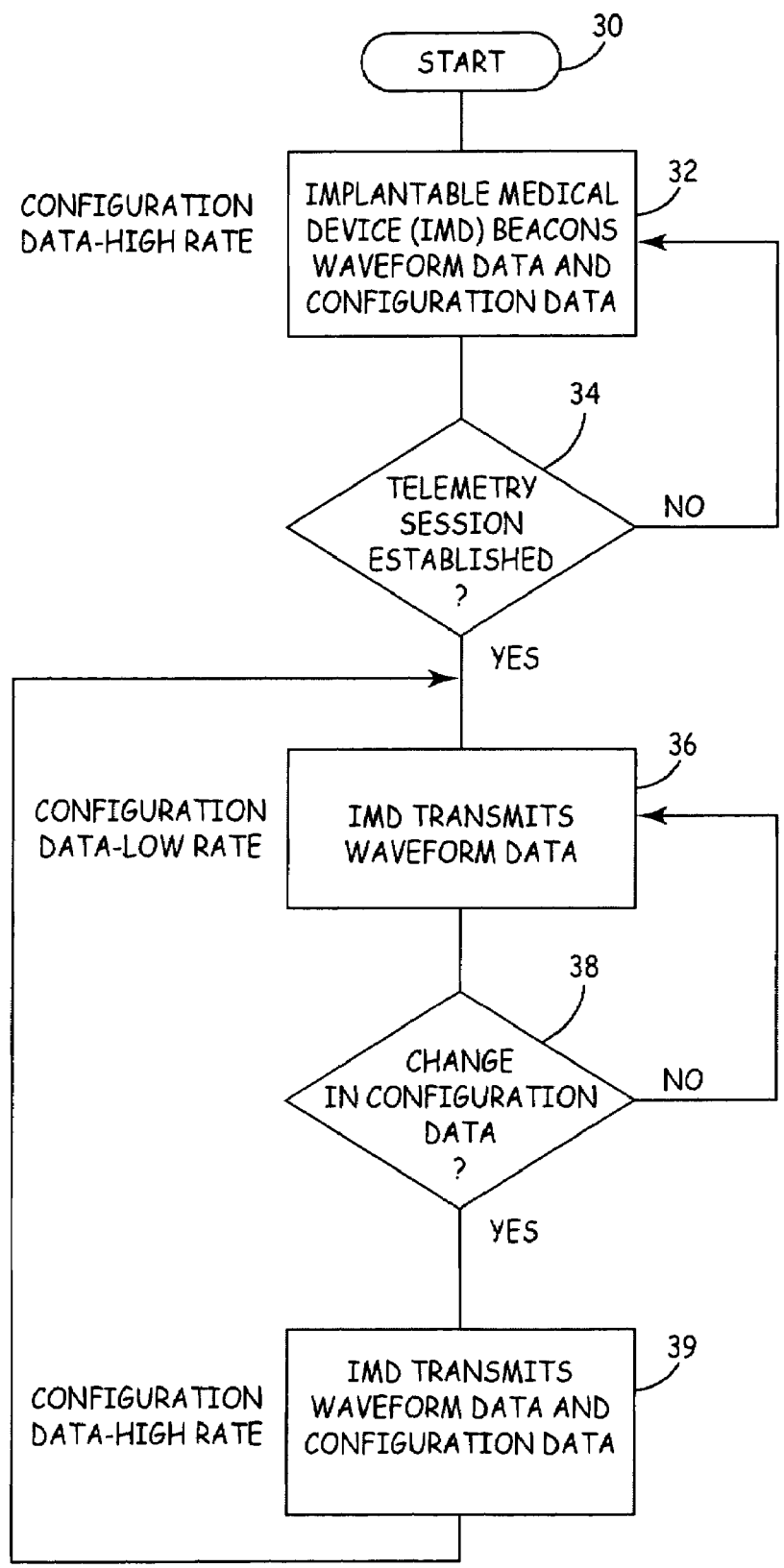
FIG. 2 is a flow diagram illustrating the basic communication scheme of the present invention.

FIG. 2 is a flow diagram illustrating the basic communication scheme of the present invention. Communication by an IMD begins at Start block 30, initiated by the presence of a magnet, an instrument downlink request, or some other initiation mechanism. Upon initiation of communication, the IMD transmits, or "beacons," waveform data and configuration data as indicated at block 32. During this beaconing stage, configuration data is transmitted at a relatively high rate (frequency of occurrence), such as once per second in an exemplary embodiment. The beaconing stage continues until a telemetry session is established between the IMD and the external processing unit, as indicated by decision block 34. Once telemetry has been established, the IMD continues to transmit waveform data according to the configuration that has been previously communicated, as indicated at block 36. Configuration data may be transmitted occasionally from the IMD to the external processing unit in this stage, but at a lower rate than during the beaconing stage. The IMD continues to transmit waveform data until a change in configuration is desired, as indicated at decision block 38. When a change in configuration is to occur, the IMD transmits waveform data according to the new configuration and transmits configuration data to the external processing unit, as indicated at block 39. The new configuration data is again transmitted at a relatively high rate in order to ensure that it is received properly by the external processing unit. After the configuration has been successfully changed, the IMD transmits waveform data having characteristics that correspond to the new configuration, as indicated at block 36.

The physical beaconing transmission by the IMD is accomplished in the same manner as for previous systems, where IMDs beaconed only basic device identification information. The system of the present invention allows the IMD to beacon essentially all of its information, by transmitting device identification information, waveform data, and configuration information that describes the waveform data being transmitted.

The communication of configuration information by the IMD is particularly useful in an ambulatory setting, where the external processing unit is a monitor that is only capable of receiving transmissions from the IMD and storing data, and is not capable of transmitting information back to the device. In fact, some monitors do not even have the ability to process the data received from the IMD, but simply store (or immediately transfer) the data received for later processing and/or display by a separate system component (which serves as the external processing unit in this type of system). While this type of limited monitoring is not typical for most clinic-based medical data communication systems, there are some applications in which such an ambulatory monitor may be employed, such as an in-home monitor that receives data from an IMD and transmits the data over a communication network for review by a caregiver at a remote location.

In the ambulatory setting, telemetry sessions are not necessarily "established" in the manner described in block 34 of FIG. 2. Thus, the IMD transmits configuration information at a constant (high) rate, rather than reducing the rate after establishment of a telemetry session. In prior ambulatory monitoring systems, the external processing unit needed to be pre-configured to receive a particular kind of data from an IMD or monitor, to ensure that the external processing unit was running an application program that could process and display the data. Any changes in the data characteristics (data type, structure or format) required re-configuration before the new data could be displayed, or interrogation of the IMD afterward to determine what data configuration changes had occurred. By transmitting configuration information from the IMD that describes the data being transmitted, a monitor is able to store the data and its associated configuration information, and an external processing unit can display all data that it understands, dynamically adjusting to different data characteristics without the need for re-configuration.

Figure 3:
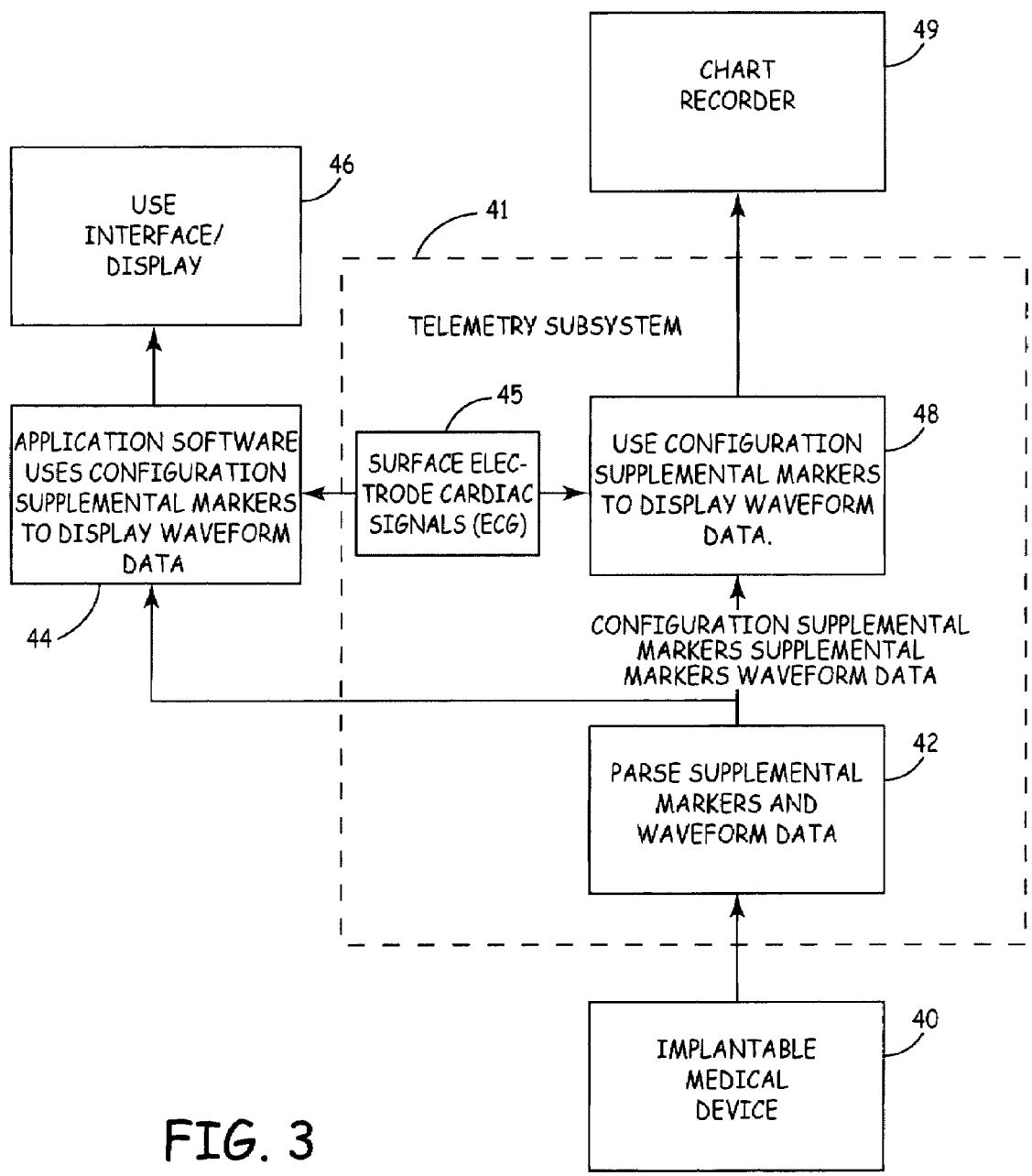
FIG. 3 is a functional block diagram illustrating a system for communication between an implantable medical device and an external processing unit in the manner described with respect to FIG. 2.

FIG. 3 is a functional block diagram illustrating an exemplary system for communication between IMD 40 and an external processing unit, in the manner described above with respect to FIG. 2. The functional block diagram of FIG. 3 includes blocks that represent actual components and signals (IMD 40, telemetry subsystem, 41, surface electrode cardiac signals 45, user interface/display 46, chart recorder 49) and functional blocks that represent software or other circuitry that is configured to perform certain functions (functional blocks 42, 44 and 48).

IMD 40 communicates all telemetry data with telemetry subsystem 41, which may be incorporated into the external processing unit or may be a separate communication module. Telemetry subsystem 41 parses the data received from implantable device 40, as indicated by functional block 42. The data received from implantable device 40 includes waveform data representing cardiac signals, markers indicating the occurrence of particular cardiac or device events, and markers that include configuration information. The markers are referred to as "supplemental markers," which are data records within a frame of transmitted data that have been used in the past to mark and describe cardiac events or to mark particular moments in time. The present invention utilizes a new type of supplemental marker (a configuration supplemental marker), in a format similar to existing supplemental markers so that it is able to be parsed by existing systems, that conveys configuration information relating to the waveform data transmitted by the IMD. The parsed data is then utilized by application software, as indicated by functional block 44, to properly display the waveform data. Specifically, the event and configuration supplemental markers are used to properly label the waveform data and to display the waveform data in an appropriate format. The application software also is able to receive data from another source, such as surface electrode cardiac (ECG) signals 45, to provide a display on user interface 46 that includes the data from implantable device 40 as well as the ECG signals.

The parsed data from functional block 42 is also utilized to display waveform data on chart recorder 49, as indicated at functional block 48. Similar to the application software (functional block 44), the event and configuration supplemental markers are used to properly label the waveform data and to display the waveform data in an appropriate format. ECG signals 45 are also utilized, to provide a display on chart recorder 49 (or any real-time storage or display device) that includes the data from implantable device 40 as well as the ECG signals.

In order to support the transmission of configuration information from the IMD, accommodations in the communication packet format are made. Generally speaking, the IMD transmits data to the telemetry subsystem associated with an external processing unit in fixed data windows (also referred to as communication frames), so that communication can occur in a structured manner. These windows include large reserved bandwidth for supplemental markers and accommodate the additional supplemental markers for configuration information according to the present invention. An exemplary data window for communication of data (including configuration information) by an IMD is shown below in Table 1.

TABLE 1

| Waveform Packet | Reserved Arbitration Bandwidth | Supplemental Markers |
|---|---|---|
| | | Configuration Information    Events |

The waveform packet includes the cardiac data measured by the implantable device, and also will indicate when a change to configuration information associated with the data occurs, by including a configuration identification number that corresponds to a configuration number of the supplemental marker that described the most up to date configuration. The configuration identification number is located at the end of the waveform packet, as the last data byte. This allows the implantable device to begin sending waveform data immediately, before the entire waveform packet is constructed (e.g., before it is known whether there are configuration supplemental markers). Also, if the construction of the waveform packet changes, the configuration byte will still be identifiable at the end of the packet. In an alternative embodiment, the supplemental markers, including configuration information and/or events, may be transmitted before the waveform packet; it will be understood by those skilled in the art that various arrangements of the data window are possible. An example of a suitable waveform packet construction is shown below in Table 2.

TABLE 2

| Data | Length | Minimum length | Maximum length |
|---|---|---|---|
| Channel 1 data | 8 bytes (always configured) | 8 bytes | 8 bytes |
| Channel 2 data | 8 bytes (always configured) | 8 bytes | 8 bytes |
| Channel 3 data | 8 bytes (if configured) | 0 bytes | 8 bytes |
| Channel 4 data | 8 bytes (if configured) | 0 bytes | 8 bytes |
| Marker Data | 12 bytes (always configured) | 12 bytes | 12 bytes |
| Configuration Byte | 1 bytes | 1 bytes | 1 bytes |
| Total | | 29 bytes | 45 bytes |

The configuration byte consists of four bits reserved for future use (for example, to indicate the type of implantable device) and four bits used for the configuration identification number.

The configuration supplemental markers (CSMs) transmitted by the implantable device contain the information needed to decode the waveform data transmitted by the device in the waveform packets. The information contained in the CSMs may or may not be different for different types of implantable devices; the CSMs are tied to the waveform data characteristics, not the device type. The CSMs are transmitted during a communication session between the implantable device and an external processing unit on the order of once per second, unless a condition is present that dictates more or less frequent transmission. These conditions include the presence of a magnet and a recent change to any of the configuration information, for example. CSMs are transmitted in their entirety, rather than only transmitting information that changed from the last CSM, so that there is no danger of error should a previous CSM have been missed by the external processing unit. CSMs also have an identification associated with them that identifies these types of markers uniquely from other types of event supplemental markers that have been used in previous telemetry systems, so that the external processing unit can properly recognize CSMs separately from other supplemental markers.

Typically, CSMs are transmitted as the first supplemental marker in the supplemental marker window, as shown above in Table 1. However, it should be understood that the CSMs may be given a lower priority in some applications, and may occur later in the supplemental marker window.

One benefit of transmitting configuration information in a CSM is that configuration information can be sent at relatively infrequent intervals. This saves communications bandwidth and device battery power, both of which are at a premium in some applications. While it is also possible to transmit configuration information with every item of data that is transmitted, throughput would be decreased in such a system compared to the system that employs CSMs as described herein.

In one embodiment, the CSMs convey information in a tag/value protocol. Each piece or group of pieces of configuration information is represented by a tag. The implantable device knows all the tags and values it can generate, and the external processing unit knows the superset of all the tags that any implantable device with which it is compatible can generate. The tag is the key used by the external processing unit and its associated software to decode the value that follows the tag. When a new tag is created, the portions of the software dealing with the old tags do not need to change, and therefore do not need to be retested. A new tag ID can just be added to the code. In this way, the external processing unit software can be modularized to minimize the impact of future changes. This reduction of the testing burden means that the external processing unit software can simply be updated when a new IMD application is released. This provides superior flexibility over a system in which the data configuration information is hard coded. The flexibility of the tag approach also allows future modifications to be easily accommodated, and relieves software developers from having to determine all possible configuration information that may at some point in the future be useful or desirable to support.

Tags describing configuration data are placed in CSMs (rather than in the waveform packet itself) at least in part because of the flexible length of supplemental markers. The impact on the waveform data in the waveform packet is minimized by communicating configuration information in a separate type of packet. This is particularly important in systems where the hardware constructs the waveform packet in such a way that there is virtually no ability to vary the length of the waveform packet.

In describing the configuration of waveform data, there are some natural groupings that all applications, present and future, typically need to specify. For example, it is almost always necessary to specify the source, gain, and sampling rate of each channel. The number of tags that are used can be minimized by grouping some of these characteristics together in the same tag. If data provided by future devices requires the groupings to be separated, that can be done as well.

Each CSM includes a supplemental marker header and at least one tag. The supplemental marker header is similar to the marker headers that have been used in existing products, so that the telemetry system is able to recognize it as a supplemental marker header and parse its identification information.

If the external processing unit receives a tag from an implantable device that it does not understand, the tag is ignored. Thus, data from an implantable device that is understood can be displayed, even when the external processing unit does not support all of the functionality of the particular implantable device that is employed.

The following tables describe examples of particular tags that might be used in a typical system.

Tag 0 (contains configuration ID that links the supplemental marker to the waveform packet B will always be in the configuration supplemental marker)

| Description | Tag ID | Length | Type of Bit Level Translation Table | Notes |
|---|---|---|---|---|
| Configuration ID Tag | 0 | 1 byte | Integer | |

Tag 0 (contains configuration ID that links the supplemental marker to the waveform packet B will always be in the configuration supplemental marker)

| Description | Tag ID | Length | Type of Bit Level Translation Table | Notes |
|---|---|---|---|---|
| Configuration ID Number | | 1 byte | Integer | First 4 bits reserved, second 4 bits represent configuration ID (changes every time configuration changes) |
| Standard Version | | 1 byte | Integer | Indicates system protocol version, to specify how supplemental markers are to be parsed |

Tag 1 (contains information that is basic to the implantable device, and can't change within a session B allows telemetry system to parse waveform packet)

| Description | Tag ID | Length | Type of Bit Level Translation Table | Notes |
|---|---|---|---|---|
| General Data Config Tag | 1 | 1 byte | Integer | |
| Number of Channels | | 4 bits | Integer | |
| Master Sampling Rate | | 2 bytes | Hertz (numeric) | Sampling rate of all channels, if common. Used as default in absence of specific sampling rate for each channel. |
| Total # of Data Samples in Waveform Packet | | 1 byte | Integer | Does not include the markers. |
| Bytes of Marker Data | | 1 byte | Integer | |
| Marker Scheme | | 4 bits | Lookup Index | Specifies marker characteristics, such as where markers are located in waveform packet, how markers are aligned to data samples, keys for decoding marker values, whether marker bytes per packet are fixed or variable, etc. |

Tag X (created for each channel, where channels have individualized characteristics)

| Description | Tag ID | Length | Translation Table | Type of Bit Level Notes |
|---|---|---|---|---|
| General Channel Config Tag | X | 1 byte | Integer | |

-continued

Tag X (created for each channel, where channels have individualized characteristics)

| Description | Tag ID | Length | Type of Bit Level Translation Table | Notes |
|---|---|---|---|---|
| Subsampling Rate of Channel | | | Hertz | |
| Channel Number | | | Integer | |
| Packed/Non-packed Data Scheme | | | Boolean | Are there empty spots (non-packed) or not (packed) in the subsampling? |

Tag 2 (general tag to describe basic channel parameters)

| Description | Tag ID | Length | Type of Bit Level Translation Table | Notes |
|---|---|---|---|---|
| Channel Device Basics Tag | 2 | 1 byte | Integer | |
| Channel Number | | 4 bits | Integer | |
| Source Name | | 12 bits | Lookup index | Link to a table of strings |
| Amplifier Gain (value) | | 20 bits | Numeric | May also need to include offset for channels providing pressure data, or the high pass filter pole of a channel. |
| Amplifier Gain (exponent) | | 1 byte | Numeric | The multiplier for waveform data to yield the actual data value. Includes one bit for sign. |
| Units | | 12 bits | Lookup index | Based on the type of data (pressure, temperature, voltage, etc.) |

Tag 3 (a generic tag used to describe basic display parameters for a channel)

| Description | Tag ID | Length | Type of Bit Level Translation Table | Notes |
|---|---|---|---|---|
| Channel Display Basics Tag | 3 | 1 byte | Integer | |
| Channel Number | | 4 bits | Integer | |
| Location on Screen | | X bits | Numeric | Typically in millimeters |
| Print on Strip Chart? | | 1 bit | Boolean | Yes or no. |
| Strip Chart Gain | | X bits | Numeric | |

In one embodiment, a CSM that would provide sufficient configuration information includes the following:

| | |
|---|---|
| Configuration tag (tag 0) | 3 bytes |
| General Data Configuration tag (tag 1) | 6 bytes |
| Channel Device Basics tag (tag 2) | (8 bytes per channel × 4 channels =) 32 bytes |
| Total | 41 bytes |

The present invention, as described above with respect to exemplary embodiments, provides the ability for an IMD to transmit data that is self-describing. Configuration information is transmitted by the IMD on a dynamic basis that describes the data being transmitted and that includes the information needed for an external processing unit to decode the data for proper manipulation, storage and/or display. As a result, data can be received and decoded by the external processing unit immediately after an IMD is "woken up," eliminating the need to wait for a device-specific application program to load before data can be displayed. In addition, the characteristics of the data provided by the IMD can be adjusted dynamically, based on conditions of the data itself, time or other factors, without the need for the external processing unit to initiate such a change. This flexibility is useful for ambulatory monitoring as well, such as an in-home monitoring system.

The present invention may find application in a wide variety of scenarios involving communication between an IMD and an external processing unit. The ability of the IMD to transmit data that is self-describing, so that it can be recognized and interpreted without pre-configuration of the receiving device, allows a number of potential situations to be readily handled. For example, dynamic changes in the characteristics of data being transmitted by the IMD are recognized by the external processing unit by virtue of the configuration information that the IMD transmits along with the data. Changes to characteristics or parameters of the data, such as the type, structure or format of the data, are reflected on the display of the external processing unit nearly instantaneously. Data is displayed properly even when interruptions in telemetry occur, due to the IMD's transmission of configuration information with its data. The external processing unit adjusts its display in response to configuration information that is received with the data, rather than simply making a change in response to a request for a data characteristic change. Basic data (e.g., waveform data) is interpreted by an external processing unit for display even when an application program specific to the IMD or data characteristics is not available. A generic waveform display instrument, such as a hand-held personal data administrator, personal digital assistant (PDA), program, or the like, is usable with the present invention to allow the user to see waveforms and associated labels for any implantable device.

Portions of the above description include specific details that are provided in order to clearly illustrate the principles of the present invention, but which should not be understood as limitations of the present invention. For example, a tag and value protocol is described to illustrate a possible implementation of a system in which an IMD transmits configuration information to an external processing unit that identifies cardiac data. Those skilled in the art will appreciate that other approaches may be used to accomplish this function, while retaining at least some of the benefits described herein. In addition, an exemplary data window has been described in which waveform data packets and supplemental markers are transmitted by an IMD. It should be understood that other configurations of data windows may be implemented that could include the same or similar data that is communicated according to the present invention, and the present invention should not be understood as limited to the particular data structure disclosed herein. Other variations from the embodiments disclosed, while achieving the purposes and principles of the present invention, will be apparent to those skilled in the art.

The description above has also typically described data transmitted by the IMD as waveform data. While this description is appropriate for most types of data, which are displayed as a waveform on the display of an external processing unit, there may be some types of data that are displayed in another manner and therefore might not be referred to as waveform data. Thus, as used herein, the term "waveform data" should be understood to include any type of data transmitted by the IMD that represents characteristics and parameters that are measured or otherwise determined by the device, and this data may also be referred to more broadly as "device data" or "medical data."

Although the present invention has been described with reference to preferred embodiments, workers skilled in the art will recognize that changes may be made in form and detail without departing from the spirit and scope of the invention.

The invention claimed is:

1. A method for communicating between an implantable medical device (IMD) and an external processing unit, the method comprising:
   transmitting device data and configuration information from the IMD;
   processing the device data for display at the external processing unit based on the configuration information; and
   notifying the external processing unit of a change to characteristics of the device data by transmitting the changed device data and updated configuration information from the IMD, wherein the external processing unit uses a single central processing unit to both execute a desktop application for processing at least some of the device data as it is received from the IMD and load an active program for execution in response to the configuration information received from the IMD, wherein transmitting device data and configuration information from the IMD and notifying the external processing unit of a change to the characteristics of the device data comprises transmitting device data in a first data packet; and transmitting configuration information in a second data packet, wherein the configuration information is structured as at least one tag having a tag identifier and at least one value representing a data parameter.

2. The method of claim 1, wherein the first data packet and the second data packet are transmitted in a common communication frame.

3. The method of claim 1, wherein transmitting device data and configuration information from the IMD and notifying the external processing unit of a change to the characteristics of the device data further comprises:
   transmitting markers that provide information to label the device data for display.

4. The method of claim 1, wherein the at least one tag is selected from a plurality of predefined tags, each of the predefined tags including a plurality of values representing data parameters that are grouped together in the predefined tag.

5. The method of claim 1, wherein processing the device data for display at the external processing unit based on the configuration information includes processing the device data for display on a chart recorder.

6. A method for communicating between an implantable medical device (IMD) and an external processing unit, the method comprising:
   transmitting device data and configuration information from the IMD;
   processing the device data for display at the external processing unit based on the configuration information; and
   notifying the external processing unit of a change to characteristics of the device data by transmitting the changed device data and updated configuration information from the IMD, wherein the external processing unit uses a single central processing unit to both execute a desktop application for processing at least some of the device data as it is received from the IMD and load an active program for execution in response to the configuration information received from the IMD, wherein transmitting device data and configuration information from the IMD and notifying the external processing unit of a change to the characteristics of the device data comprises transmitting device data in a first data packet; and transmitting configuration information in a second data packet, wherein the first and second data packets include a configuration identifier correlating the device data with the configuration information.

7. A method for communicating between an implantable medical device (IMD) and an external processing unit, the method comprising:
   transmitting configuration information from the IMD;
   transmitting device data from the implanted medical device, the device data including an indicator of the configuration information that is to be associated with the device data;
   comparing, at the external processing unit, the configuration information most recently received from the IMD to the indicator in the device data of the configuration information that is to be associated with the device data; and
   processing the device data based on the configuration information, upon determining that the configuration information most recently received from the IMD corresponds to the indicator in the device data of the configuration information that is to be associated with the device data;
   transmitting device data, including the indicator of the configuration information that is to be associated with the device data, in a first data packet; and
   transmitting configuration information in a second data packet.

8. The method of claim 7, wherein the first data packet and the second data packet are transmitted in a common communication frame.

9. The method of claim 7, wherein transmitting configuration information and device data from the IMD further comprises:
   transmitting markers that provide information to label the device data for display.

10. The method of claim 7, wherein the configuration information is structured as at least one tag having a tag identifier and at least one value representing a data parameter.

11. The method of claim 10, wherein the at least one tag is selected from a plurality of predefined tags, each of the predefined tags including a plurality of values representing data parameters that are grouped together in the predefined tag.

12. A method for communicating between an implantable medical device (IMD) and an external processing unit, the method comprising:

initiating communication by the IMD;

transmitting device data and configuration information from the IMD in a beaconing procedure, the configuration information being transmitted at a first rate;

determining whether the configuration information is to be changed; and upon determination that the configuration information is to be changed, transmitting device data and configuration information from the IMD in a manner where the configuration information is transmitted at the first rate during transmission of device data and configuration information from the IMD in the beaconing procedure, determining whether a telemetry session has been established between the IMD and the external processing unit; and upon determination that a telemetry session has been established between the IMD and the external processing unit, transmitting device data and configuration information from the IMD in a manner where the configuration information is transmitted at a second rate lower than the first rate.

* * * * *